(12) United States Patent
Ho

(10) Patent No.: US 9,345,903 B2
(45) Date of Patent: May 24, 2016

(54) DEVICE FOR INCREASING ENERGY AT ACUPUNCTURE POINTS

(71) Applicant: Nien-Chung Pan, New Taipei (TW)

(72) Inventor: Ko-Liang Ho, New Taipei (TW)

(73) Assignee: NIEN-CHUNG PAN, New Taipei (TW)

( * ) Notice: Subject to any disclaimer, the term of this patent is extended or adjusted under 35 U.S.C. 154(b) by 0 days.

(21) Appl. No.: 14/522,745

(22) Filed: Oct. 24, 2014

(65) Prior Publication Data

US 2015/0246241 A1    Sep. 3, 2015

(30) Foreign Application Priority Data

Mar. 3, 2014    (TW) .............................. 103203594 U

(51) Int. Cl.
*A61N 5/06*    (2006.01)

(52) U.S. Cl.
CPC ....... *A61N 5/0619* (2013.01); *A61N 2005/0632* (2013.01); *A61N 2005/0643* (2013.01); *A61N 2005/0662* (2013.01)

(58) Field of Classification Search
CPC ...................................................... A61N 5/06
See application file for complete search history.

(56) References Cited

U.S. PATENT DOCUMENTS

| | | | | |
|---|---|---|---|---|
| 1,421,756 A * | 7/1922 | Arnao | .................... | A61N 5/06 4/537 |
| 1,554,304 A * | 9/1925 | Steinberg | ............. | A61N 5/0603 250/503.1 |
| 1,622,142 A * | 3/1927 | Girard | .................... | A61N 5/06 362/269 |
| 2,954,771 A * | 10/1960 | Boyan | .................... | A61N 5/01 250/504 R |
| 5,698,866 A * | 12/1997 | Doiron | .................... | A61N 5/062 257/717 |
| 6,669,627 B1 * | 12/2003 | Campbell | ............ | A61N 5/0618 600/27 |
| 7,977,658 B2 * | 7/2011 | Stuba | .................... | A61B 18/18 250/504 H |
| 2004/0181268 A1 * | 9/2004 | Anderer | ............... | A61N 5/0619 607/90 |
| 2004/0212314 A1 * | 10/2004 | Nevins | .................. | A61M 21/00 315/149 |
| 2004/0230259 A1 * | 11/2004 | Di Matteo | ............ | A61N 5/0616 607/88 |
| 2005/0256554 A1 * | 11/2005 | Malak | .................. | A61N 5/0616 607/88 |
| 2005/0276042 A1 * | 12/2005 | Ho | .......................... | F21L 4/027 362/205 |
| 2006/0030908 A1 * | 2/2006 | Powell | ................. | A61N 5/0616 607/88 |
| 2006/0095099 A1 * | 5/2006 | Shanks | ................ | A61N 5/0617 607/89 |
| 2007/0213792 A1 * | 9/2007 | Yaroslavsky | ......... | A61N 5/0613 607/100 |
| 2008/0039906 A1 * | 2/2008 | Huang | ................. | A61N 5/0603 607/88 |
| 2008/0091250 A1 * | 4/2008 | Powell | .................. | A61M 21/00 607/90 |

(Continued)

*Primary Examiner* — Lynsey Crandall
(74) *Attorney, Agent, or Firm* — Li&Cai Intellectual Property (USA) Office

(57) ABSTRACT

A device for increasing energy at acupuncture points includes a housing, a light-emitting module, a base, a circuit device, a bending tube and a connection unit. The light-emitting module is disposed in the housing and has a plurality of light-emitting units. The base is a hollow casing. The circuit device includes a circuit board disposed in the base and electrically connected to a first connector. One end of the bending tube is connected to the housing. A transmission line is disposed in the bending tube. One end of the transmission line is electrically connected to the light-emitting module. The other end of the bending tube has a second connector electrically connected to the other end of the transmission line. The other end of the bending tube is removably connected to the base through the connection unit. The first connector and the second connector are selectively electrically connected.

8 Claims, 4 Drawing Sheets

(56) References Cited

U.S. PATENT DOCUMENTS

| | | | | |
|---|---|---|---|---|
| 2008/0096156 A1* | 4/2008 | Rose | ................ | A61C 1/0015 |
| | | | | 433/29 |
| 2009/0254155 A1* | 10/2009 | Kanarsky | ............ | A61N 5/0613 |
| | | | | 607/89 |
| 2010/0286576 A1* | 11/2010 | Pryor | ................ | A61H 21/00 |
| | | | | 601/18 |
| 2011/0178583 A1* | 7/2011 | Gerlitz | ............... | A61N 5/0616 |
| | | | | 607/89 |
| 2011/0232577 A1* | 9/2011 | Ryan | ................ | A01K 1/0218 |
| | | | | 119/28.5 |
| 2013/0238060 A1* | 9/2013 | Nevins | ............... | A61N 5/0613 |
| | | | | 607/90 |
| 2013/0274840 A1* | 10/2013 | McLeod | ............... | A61F 7/00 |
| | | | | 607/100 |

\* cited by examiner

DEVICE FOR INCREASING ENERGY AT ACUPUNCTURE POINTS

BACKGROUND OF THE INVENTION

1. Field of the Invention

The present disclosure relates to a device for increasing energy at acupuncture points; in particular, to a non-invasive photodynamic therapy equipment which emits light having nanometer wavelengths.

2. Description of Related Art

In recent years, the medical field has turned to using photodynamic therapy. Energy from light is used to treat skin disease, remove black spots on skin, induce hair growth, etc. In photodynamic therapy, photosensitizers are applied on a region to be healed and then excited by light or laser. The photosensitizer excited by light undergoes photochemical reaction, producing a healing or stimulating effect.

Photodynamic therapy equipment on the current market uses mainly two types of techniques, including laser light and pulsed light. Laser is limited by wavelength and other characteristics, so it can only treat skin conditions at deep layers. Laser has high energy which leads to short treatment time, and can carry a definite amount of risk and needs to be operated by skilled technicians. Pulsed light is used to stimulate the regeneration of skin collagen. During treatment, the patient does not need to avoid sunlight. Pulsed light does not affect daily life, but it can only treat skin conditions at shallow layers, and is relatively ineffective at treating skin conditions at deep layers. Equipment for the two kinds of techniques are costly, such that the cost for photodynamic therapy is currently expensive, and using lasers of different wavelengths for different treatments increases the complexity of the equipment.

Hence, the present inventor believes the above mentioned disadvantages can be overcome, and through devoted research combined with application of theory, finally proposes the present disclosure which has a reasonable design and effectively improves upon the above mentioned disadvantages.

SUMMARY OF THE INVENTION

The object of the present disclosure is to provide a device for increasing energy at acupuncture points, which has a lower production cost, emits non-dangerous light energy, is operable by common technicians, has a long life span and is easy to maintain.

Another object of the present disclosure is to provide a device for increasing energy at acupuncture points, whose electric circuit is easily replaceable, facilitating maintenance.

In order to achieve the aforementioned objects, the present disclosure provides a device for increasing energy at acupuncture points, including: a housing; a light-emitting module disposed in the housing having a plurality of light-emitting units which are LEDs; a base which is a hollow casing; a circuit device including a circuit board disposed in the base and electrically connected to a first connector; a bending tube, wherein one end of the bending tube is connected to the housing, the interior of the bending tube has a transmission cable, one end of the transmission cable is electrically connected to the light-emitting module, the other end of the bending tube has a second connector, and the second connector is electrically connected to the other end of the transmission cable; and a connection unit, wherein the other end of the bending tube is removably connected to the base through the connection unit, and the first connector and the second connector are selectively electrically connected.

The present disclosure has at least the following advantages. The light-emitting unit of the present disclosure is an LED, such that the device for increasing energy at acupuncture points is more practical and has a lower production cost. Additionally, the device for increasing energy at acupuncture points of the present disclosure has a light source that is not dangerous and can be operated by common technicians. The life span of the LED is long and stable, maintenance is convenient, the position and angle can also be adjusted by the user and is very convenient to use.

The other end of the bending tube of the device for increasing energy at acupuncture points of the present disclosure is removably connected to the base by a connection unit, such that the bending tube and the base can be separated, and the electrical connection between the first connector and second connector can be separated as well. Therefore when the circuit device is damaged, the base and the circuit device can be removed and individually repaired, facilitating repair and replacement of components.

In order to further the understanding regarding the present disclosure, the following embodiments are provided along with illustrations to facilitate the understanding of the present disclosure.

DETAILED DESCRIPTION OF THE PREFERRED EMBODIMENTS

Figure 1:
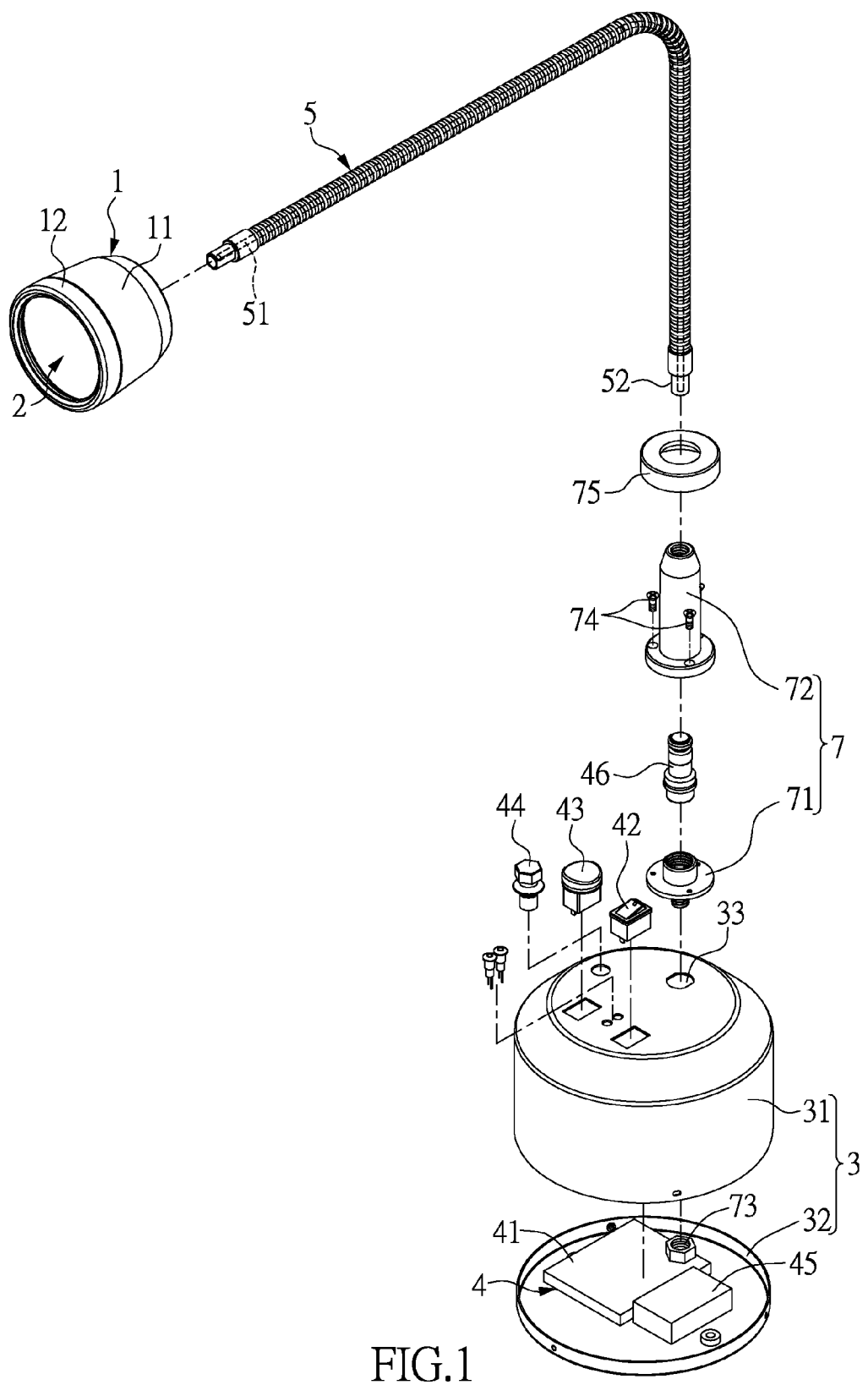
FIG. 1 shows an exploded view of a device for increasing energy at acupuncture points according to the present disclosure.
Figure 2:
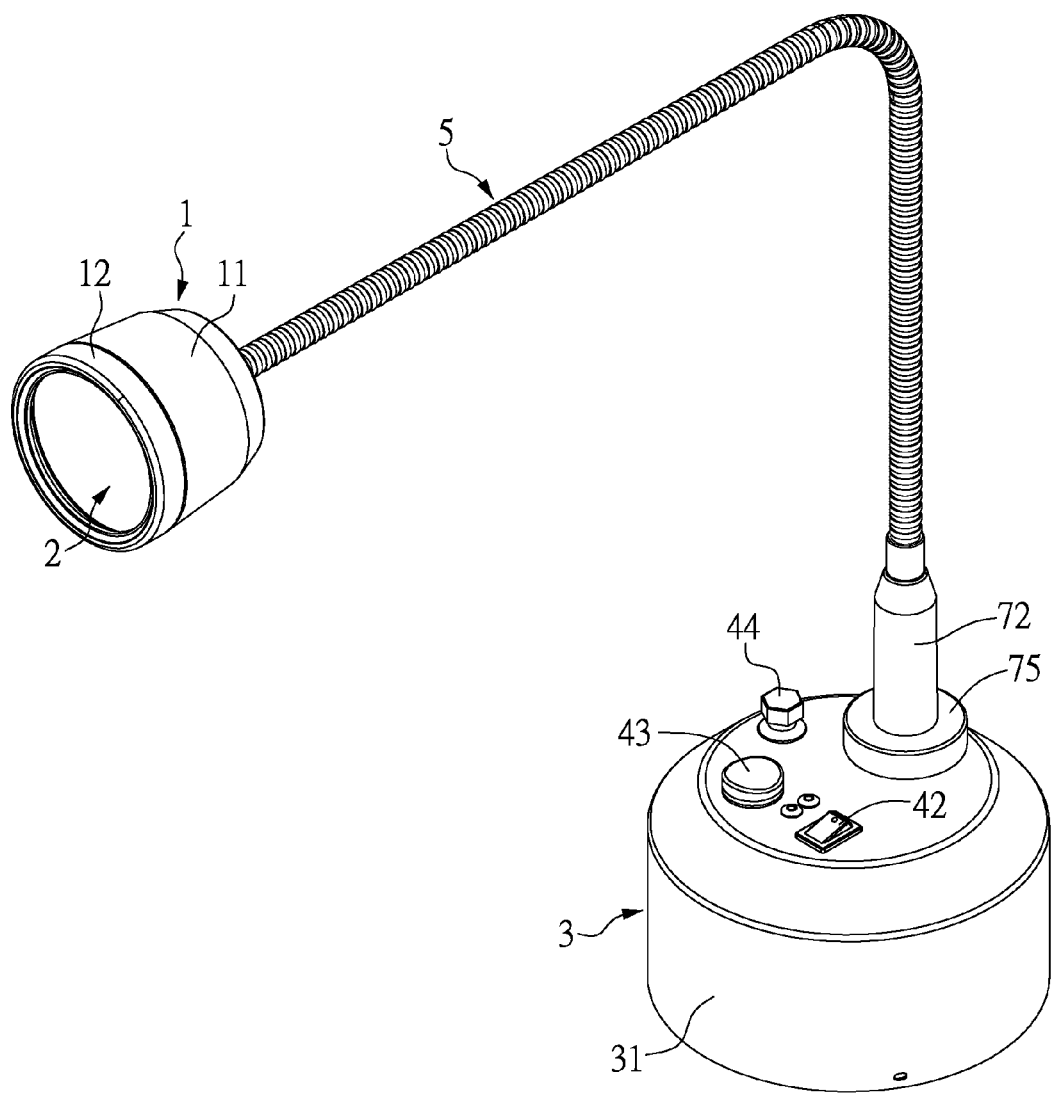
FIG. 2 shows a perspective view of an assembled device for increasing energy at acupuncture points according to the present disclosure.
Figure 3:
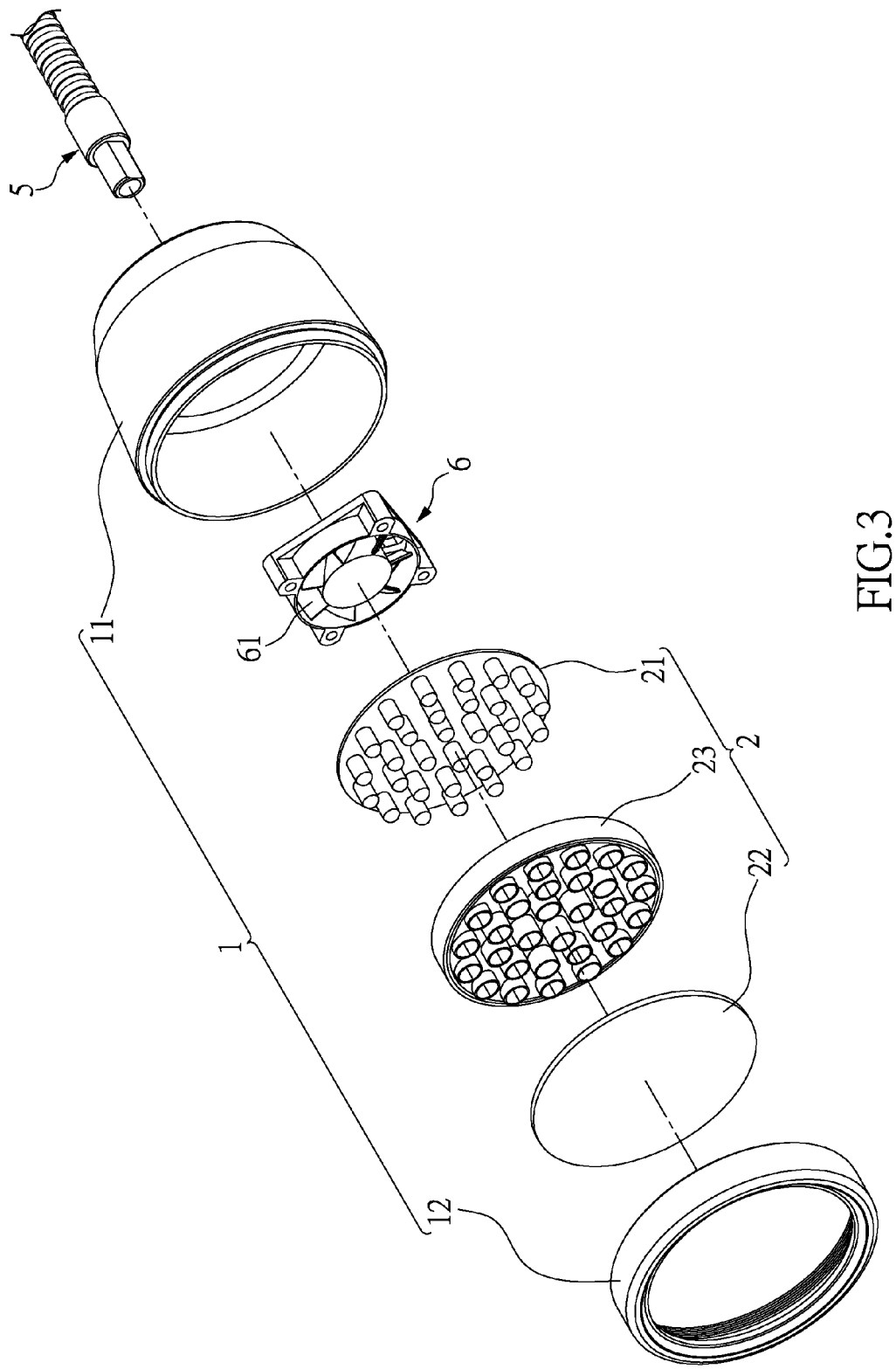
FIG. 3 shows an exploded view of a portion of a device for increasing energy at acupuncture points according to the present disclosure.

Referring to FIG. 1 to FIG. 3, the present disclosure provides a device for increasing energy at acupuncture points, in particular, to a non-invasive photodynamic therapy equipment which emits light having nanometer wavelengths and includes a housing 1, a light-emitting module 2, a base 3, a circuit device 4, a bending tube 5 and a connection unit 7.

The housing 1 is a hollow casing whose shape and structure is not limited. The housing 1 can be a one-piece, a two-piece or a multi-piece structure. In the present embodiment the housing 1 includes a lamp holder 11 and a front cover 12. The lamp holder 11 is a hollow casing whose front end is open. The front cover 12 is annular and is disposed at the front end of the lamp holder 11. The lamp holder 11 and the front cover 12 can be connected by latch, screw or adhesive. The lamp holder 11 and the front cover 12 define an accommodating space therebetween. The rear end of the lamp holder 11 can have a plurality of heat dissipating holes (not shown in the figures).

The light-emitting module 2 is disposed in the housing 1. The light-emitting module 2 has a plurality of light-emitting units 21. The light-emitting units 21 can produce at least one type of visible light, and can further include a translucent unit 22 and a reflector 23. The translucent unit 22 adheres to the front cover 12 of the housing 1. The reflector 23 is disposed between the translucent unit 22 and the light-emitting unit 21. The reflector 23 can reflect light from the light-emitting units 21 to obtain a greater lamination area. The translucent unit 22 is made of glass and can protect the light-emitting units 21. The surface of the translucent unit 22 can have a UV resistant coating for preventing damage to the human body by ultraviolet light. However, the form and structure of the light-emitting module 2 is not limited. For example, the light-emitting units 21 can produce one, three or four types of visible light, and the UV resistant coating or the reflector 23 can be omitted.

The present disclosure can further include a heat dissipating module 6. The heat dissipating module 6 can include a fan 61, a heat sink (not shown in the figures), etc. The heat dissipating module 6 is disposed in the housing 1 and behind the light-emitting module 2 for dissipating heat produced by the light-emitting module 2. The housing 1, the light-emitting module 2 and the heat dissipating module 6 can be packaged to form a lighting module.

The base 3 is a hollow casing whose shape and structure is not limited. The base 3 can be a one-piece, a two-piece or a multi-piece structure. In the present embodiment the base 3 includes an upper base 31 and a lower base 32. The upper base 31 and the lower base 32 can be connected by latch, screw or adhesive, thereby forming the base 3.

The circuit device 4 includes a circuit board 41, and can further include a power switch 42, a function switch 43 and a charging switch 44. The circuit board 41 is disposed in the base 3 and can be connected to the appropriate power source for inputting the required power. The power switch 42, function switch 43 and charging switch 44 are disposed on the base 3 and are electrically connected to the circuit board 41. The circuit device 4 is electrically connected to the light-emitting module 2 and the fan 61 of the heat dissipating module 6 for controlling the light-emitting module 2 and the fan 61. The function switch 43 can provide the user the ability to select the mode of operation, including continuous lighting, timed lighting and termination of lighting.

Additionally, the present disclosure can further have a light source switch (not shown in the figures) for switching the light-emitting units 21. The light-emitting units 21 include two or more colors of visible light, each having specific treatment effects. For example, the light-emitting units 21 are LEDs and can include red LED having wavelength of 600 to 700 nanometers, blue LED having wavelength of 400 to 450 nanometers, green LED having wavelength of 520 to 540 nanometers, yellow LED having wavelength of 580 to 590 nanometers. The LEDs can be arranged in array on the light-emitting module 2, or arranged in rings on the light-emitting module 2.

The circuit device 4 can further include a power charger (not labeled) disposed on the circuit board 41 provided with a rechargeable battery 45 electrically connected to the circuit board 41. The charging switch 44 can be used by the user to control the power charger on the circuit board 41 such that an external power supply (not labeled) can charge the rechargeable battery 45. The rechargeable battery 45 is disposed in the base 3. When the external power supply stops providing power, the rechargeable battery 45 can provide power to all units of the present disclosure which use electricity. Additionally, the circuit device 4 can further include a timer (not labeled). The timer is disposed on the circuit board 41, provided for setting the time of timed lighting of the present disclosure.

The bending tube 5 is a bendable tube. One end of the bending tube 5 is connected to the housing 1. Namely, one end of the bending tube 5 can be connected to the rear end of the lamp holder 11 of the housing 1. The bending tube 5 has a transmission line 51 therein. One end of the transmission line 51 is electrically connected to the light-emitting module 2 and the fan 61 of the heat dissipating module 6, such that the circuit device 4 can be electrically connected to the light-emitting module 2 and the fan 61 of the heat dissipating module 6 through the transmission line 51.

The other end of the bending tube 5 is removably connected to the base 3 through the connection unit 7. The connection unit 7 can include a lower support unit 71 and an upper support unit 72. The lower support unit 71 is a hollow seat fixed on the base 3. The lower support unit 71 can be fixed to the base 3 by latch, screw or other methods. In the present embodiment the lower support unit 71 is inserted into a fixture hole 33 of the base 3, and then fixed to the base 3 by a screw cap 73 screwed onto the lower support unit 71. The circuit board 41 is electrically connected to a first connector 46 disposed in the lower support unit 71. The first connector 46 can be an electrical connector, plug, socket, terminal, conductive plate, or other electrical connection unit.

The upper support unit 72 is a hollow seat disposed on the lower support unit 71. The other end of the bending tube 5 is connected to the upper support unit 72. In the present embodiment, the other end of the bending tube 5 is fixedly inserted into the upper support unit 72. The other end of the bending tube 5 has a second connector 52 which is electrically connected to the other end of the transmission line 51. The second connector 52 can be an electrical connector, plug, socket, terminal, conductive plate, or other electrical connection unit. The first connector 46 and the second connector 52 are corresponding connectors and selectively electrically connected.

The lower support unit 71 and the upper support unit 72 can be removably connected. In the present embodiment, the lower support unit 71 and the upper support unit 72 are fixed by a plurality of screws 74, such that the lower support unit 71 and the upper support unit 72 are removably connected. Therefore, the other end of the bending tube 5 is removably connected to the base 3 through the connection unit 7. Of course, the lower support unit 71 and the upper support unit 72 can also be connected by latch, engagement, buckle, snap, etc. and the method of connection is not limited.

When the other end of the bending tube 5 is connected to the base 3, the first connector 46 and the second connector 52 contact each other to form an electrical connection, such that the electrical power and signal of the circuit device 4 can be transmitted to the light-emitting module 2 and the fan 61 of the heat dissipating module 6 through the transmission line 51. The upper support unit 72 can further be sleeved by a hole cover 75 for covering the screw 74 for aesthetic purposes.

Regarding the device for increasing energy at acupuncture points of the present disclosure, the user can place the light-emitting module 2 on areas of discomfort or acupuncture points of the human body, to target specific locations for treatment. The light-emitting units 21 of two or more colors of the light-emitting module 2 can be used to achieve a greater area of illumination. At the same time, through the switching of the light source, the user can select the light-emitting units 21 having the required color to achieve particular treatment effects. For example, visible red light having a wavelength between 600 and 700 nanometers can stimulate blood circulation and cell growth, thereby increasing the metabolism of the skin, and growth of skin and hair. Visible blue light having a wavelength between 400 and 450 nanometers can treat acnes. A mixture of visible red light and visible blue light can kill fungi on athletes' foot. Green LED having a wavelength between 520 and 540 nanometers can fight aging of skin and reduce wrinkles. Yellow LED having a wavelength between 580 and 590 nanometers can increase immunity and alleviate allergy. The present disclosure can stimulate blood circulation and relieve pain such as pain from cancer.

The device for increasing energy at acupuncture points of the present disclosure uses LEDs as light-emitting units, such that the device for increasing energy at acupuncture points of the present disclosure is more practical and has a lower production cost. Additionally, the light energy of the device for increasing energy at acupuncture points is not dangerous and can be operated by common technicians. At the same time, LED has a long and stable lifespan, is easy to maintain, and can be readily moved and have its angle adjusted by the user, making it very convenient to use.

Figure 4:
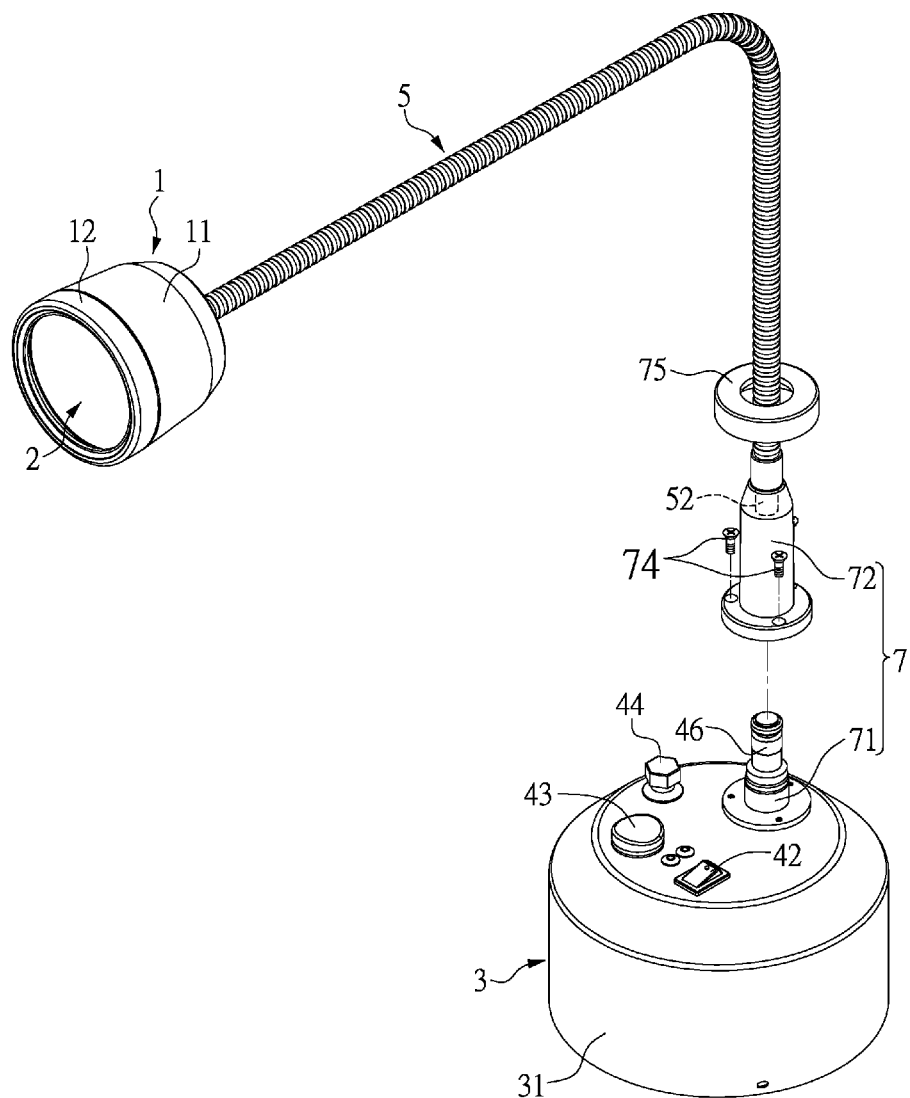
FIG. 4 shows a perspective view of a device for increasing energy at acupuncture points during removal according to the present disclosure.

Regarding the device for increasing energy at acupuncture points of the present disclosure, the other end of the bending tube can be removably connected to the base 3 through the connection unit 7, such that the bending tube 5 and the base 3 can be separated (as shown in FIG. 4), and the first connector 46 and the second connector 52 which are selectively electrically connected can also be separated. Therefore when the circuit device 4 is damaged, the base 3 and the circuit device 4 can be removed and individually repaired, facilitating the maintenance and replacement of components.

The descriptions illustrated supra set forth simply the preferred embodiments of the present disclosure; however, the characteristics of the present disclosure are by no means restricted thereto. All changes, alternations, or modifications conveniently considered by those skilled in the art are deemed to be encompassed within the scope of the present disclosure delineated by the following claims.

What is claimed is:

1. A device for increasing energy at acupuncture points, comprising:
   a housing;
   a light-emitting module disposed in the housing and having a plurality of light-emitting units, wherein the light-emitting units are LEDs;
   a base, which is a hollow casing;
   a circuit device including a circuit board, wherein the circuit board is disposed in the base and is electrically connected to a first connector;
   a bending tube, having a first end and a second end, wherein the first end of the bending tube is connected to the housing, a transmission line is disposed in the bending tube, a first end of the transmission line is electrically connected to the light-emitting module, the second end of the bending tube has a second connector, and the second connector is electrically connected to a second end of the transmission line; and
   a connection unit, the connection unit includes a lower support unit and an upper support unit, the lower support unit is fixed on the base;
   the second end of the bending tube and the second connector is inserted into the upper support unit; and the first connector is mounted on the lower support unit;
   the housing and the light-emitting module and the bending tube and the second connector and the upper support unit are grouped into a dismountable unit, and the upper support unit is removably connected to a top end of the lower support unit, thereby the dismountable unit can be separated from the base, and the first connector and the second connector are removably connected and selectively electrically connected.

2. The device for increasing energy at acupuncture points according to claim 1, wherein the lower support unit is fixed to the base through snapping or screws.

3. The device for increasing energy at acupuncture points according to claim 1, wherein the lower support unit is inserted to a fixture hole on the base, and a screw cap is screwed onto the lower support unit for fixing the lower support unit.

4. The device for increasing energy at acupuncture points according to claim 1, wherein the lower support unit and the upper support unit are connected by a plurality of screws.

5. The device for increasing energy at acupuncture points according to claim 4, wherein the upper support unit is sleeved by a hole cover, and the hole cover covers the screws.

6. The device for increasing energy at acupuncture points according to claim 1, wherein the first connector and the second connector are corresponding electrical connectors, plugs, sockets, terminals, or conductive plates.

7. The device for increasing energy at acupuncture points according to claim 1, wherein the light-emitting module includes a translucent unit and a reflector, the translucent unit adheres to the housing, the reflector is disposed between the translucent unit and the light-emitting units.

8. The device for increasing energy at acupuncture points according to claim 1, wherein the circuit device includes a power switch, a function switch, a charging switch and a rechargeable battery, the power switch, the function switch and the charging switch are disposed on the base, the rechargeable battery is disposed in the base, the power switch, the function switch, the charging switch, and the rechargeable battery are electrically connected to the circuit board.

\* \* \* \* \*